US010934519B2

(12) United States Patent
Roy et al.

(10) Patent No.: US 10,934,519 B2
(45) Date of Patent: Mar. 2, 2021

(54) SYSTEMS, METHODS AND CONTROL LAWS FOR CELL HARVESTING

(75) Inventors: Jaydeep Roy, Saratoga Springs, NY (US); Andrew Michael Leach, Clifton Park, NY (US); Weston Blaine Griffin, Niskayuna, NY (US); Stefan Rakuff, Clifton Park, NY (US); Philip Alexander Shoemaker, Scotia, NY (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 586 days.

(21) Appl. No.: 13/193,925

(22) Filed: Jul. 29, 2011

(65) Prior Publication Data
US 2013/0029411 A1    Jan. 31, 2013

(51) Int. Cl.
C12M 1/00    (2006.01)

(52) U.S. Cl.
CPC .................................. *C12M 47/02* (2013.01)

(58) Field of Classification Search
None
See application file for complete search history.

(56) References Cited

U.S. PATENT DOCUMENTS

| | | | |
|---|---|---|---|
| 5,053,334 A * | 10/1991 | Arathoon et al. | 435/226 |
| 5,597,486 A * | 1/1997 | Lutz | A23C 9/1422 |
| | | | 210/639 |
| 5,620,894 A | 4/1997 | Barger et al. | |
| 5,947,689 A * | 9/1999 | Schick | B01D 61/16 |
| | | | 210/195.2 |
| 6,350,382 B1 * | 2/2002 | Schick | B01D 61/18 |
| | | | 210/637 |
| 6,780,322 B1 * | 8/2004 | Bissler et al. | 210/637 |
| 7,790,039 B2 | 9/2010 | Bosch et al. | |
| 8,157,999 B2 * | 4/2012 | de los Reyes | B01D 61/22 |
| | | | 210/321.72 |
| 2001/0035377 A1 * | 11/2001 | Johnson | A61M 1/3621 |
| | | | 210/645 |
| 2002/0043487 A1 * | 4/2002 | Schick | B01D 61/16 |
| | | | 210/85 |
| 2002/0179544 A1 | 12/2002 | Johnson et al. | |
| 2005/0084961 A1 * | 4/2005 | Hedrick et al. | 435/366 |
| 2005/0189297 A1 | 9/2005 | Bosch et al. | |
| 2007/0246406 A1 * | 10/2007 | Dibel et al. | 210/96.2 |
| 2008/0142456 A1 | 6/2008 | Duhamel et al. | |
| 2008/0277343 A1 * | 11/2008 | Schick | 210/650 |
| 2009/0277833 A1 * | 11/2009 | Mir | B01D 61/147 |
| | | | D61/147 |
| 2011/0139723 A1 | 6/2011 | Griffin et al. | |
| 2011/0143427 A1 | 6/2011 | Griffin et al. | |
| 2012/0294836 A1 * | 11/2012 | Rowley et al. | 424/93.7 |

FOREIGN PATENT DOCUMENTS

| | | |
|---|---|---|
| CN | 1886498 A | 12/2006 |
| CN | 101258237 A | 9/2008 |
| EP | 0248675 A1 | 12/1987 |
| EP | 2380970 A1 | 10/2011 |
| JP | 6332484 A | 2/1988 |
| JP | 2003334057 A | 11/2003 |
| JP | 2007524396 A | 8/2007 |
| WO | 199850699 A1 | 11/1998 |
| WO | 99934848 A1 | 7/1999 |
| WO | 2010057318 A1 | 5/2010 |
| WO | WO 2011/091248 * | 7/2011 ............. B01D 63/02 |

OTHER PUBLICATIONS

GE-Healthcare, AKTAcrossflow, Instrument Handbook,11-012-33 AC, Sep. 2007.

Unofficial International Search Report and Written Opinion issued in connection with corresponding PCT Application No. PCT/SE2012/050757 dated Oct. 30, 2012.

Unofficial English translation of Japanese Office Action issued in connection with corresponding JP Application No. 2014-522788 dated Mar. 1, 2010.

Office Action issued in connection with corresponding CN Application No. 201280037432.9 dated Nov. 14, 2014.

European Search Report and Written Opinion issued in connection with corresponding EP Application No. 12820749.5—1501 dated Mar. 17, 2015.

* cited by examiner

*Primary Examiner* — Louise W Humphrey
*Assistant Examiner* — Srikanth Patury
(74) *Attorney, Agent, or Firm* — Eversheds Sutherland (US) LLP

(57) ABSTRACT

The methods of harvesting cells are provided, wherein the methods comprise introducing a processing material and a source material into a processing loop. The processing loop comprises a processing chamber and a filtering device. The processing material and the source material are circulating through the processing chamber and the filtering device, wherein the processing chamber has a mass; balancing an influx of the processing material into the processing chamber with a permeate flux of the filtering device to maintain the mass of the processing chamber at a constant value; and collecting the cells in a collection chamber. Cell harvesting devices are also provided for processing and harvesting cells using a control law to balance the mass of the processing chamber through the entire process.

18 Claims, 6 Drawing Sheets

| | | | |
|---|---|---|---|
| Insert | 1. | Attach bags, insert and release manual pinch values | |
| Prime | 2. | B→P→HF→P + W | |
| | 3. | S→P→HF→P + W | |
| Load | 4a. | B→S | Optional source bag rinse (n cycles). |
| | 4b. | S→P→HF→P + W | Rinse can coincide with step 4 for high volume applications |
| Volume Adjustment | 5. | P→HF→P + W | |
| Wash | 6. | B→P→HF→P + W | |
| Concentrate | 7. | P→HF→P + W | |
| | 8. | B→P→HF→C | |
| Collect | 9a. | B→P | Optional process bag rinse (n cycles) |
| | 9b. | B→P→HF→C | |
| Remove | 10. | Close manual pinch valves and remove | |

FIG. 2

SYSTEMS, METHODS AND CONTROL LAWS FOR CELL HARVESTING

FIELD

The invention relates to systems, methods and control laws for harvesting cells.

BACKGROUND

Harvesting of cells from various sources is of high demand for different therapeutic applications, such as cell therapy, or tissue engineering. The examples of therapeutic applications include but are not limited to autologous or allogeneic transplantation of stem cells, transplantation of matured functional cells, modified human cells, or xeno-transplantation of non-human cells. The applications facilitate healing of the damaged tissue or organ by regenerating cells to improve the condition of a diseased state.

For translational research, which facilitate the development and implementation of scientific discoveries to prevent, diagnose, and treat disease using state-of-the-art technologies, a range of potential cell types require isolation prior to modification, activation, and expansion. To meet this translational market need, the cells are required to be concentrated and washed to remove any impurities. For preserved cell applications, where previously separated mono-nucleated cells (MNC) are stored in cryogenic temperatures after suspension in media containing preservatives such as dimethylsulfoxide (DMSO), the cells need to be washed, typically through a dilution process, several times to minimize the preservative's concentration before re-concentrating and re-suspending the cells for use. Therefore, the processing of cryo-preserved cells is necessary before use in any application, specifically for therapeutic application or research purpose.

For both of the examples, the cells should be processed to concentrate and wash repeatedly to ensure high quality. Although various methods and systems for harvesting cells are known in the art, the quality and quantity output of these systems are insufficient for therapeutic application. Therefore, systems and methods for harvesting cells under sterile condition with processing facilities, reduced infrastructure requirements and robust operational efficiency, are highly desirable.

BRIEF DESCRIPTION

The methods and devices of the invention for harvesting cells result in high quality cell samples, which are devoid of residual impurities or preservatives. These methods and devices resolve many of the problems associated with the cells used for translational application or cells recovered from cryogenic preserved cells.

One example of the method of harvesting cells from a fluidic material in a processing loop comprises, a processing chamber and a filtering device wherein the fluidic material has a volume and the processing chamber has an overall capacity, comprises circulating the fluidic material through the processing loop and balancing an influx of the fluidic material into the processing chamber with a permeate flux of the filtering device to maintain the volume of the fluidic material in the processing chamber at a constant value, concentrating the cells by increasing the permeate flux of the filtering device relative to the influx of the fluidic material into the processing chamber; and collecting the concentrated cells in a collection chamber.

Another example of the method of harvesting cells from a fluidic material in a processing loop comprises, a processing chamber and a filtering device wherein the fluidic material has a mass and the processing chamber has an overall capacity, comprises circulating the fluidic material through the processing loop and balancing an influx of the fluidic material into the processing chamber with a permeate flux of the filtering device to maintain the mass of the fluidic material in the processing chamber at a constant value; concentrating the cells by increasing the permeate flux of the filtering device relative to the influx of the fluidic material into the processing chamber; and collecting the concentrated cells in a collection chamber.

In at least one example of the method of controlling mass of a processing chamber of a cell harvesting device comprises, a filtering device, the processing chamber, a network of input and output lines operatively coupled to a source pump, a buffer pump and a permeate pump, comprises creating an estimator for a flow rate of the permeate pump using velocity of the source pump or buffer pump, a calibration constant of the source pump or buffer pump, and the rate of change of the mass of the processing chamber; and setting a flow rate through the source pump using a control law comprising the estimator and a feedback term, wherein the feedback term comprises the rate of change of the mass of the processing chamber, a setpoint and a feedback gain, and wherein the feedback gain is greater than zero and the mass of the processing chamber is constant at the setpoint.

At least one embodiment of the cell harvesting device comprises, a processing loop comprising a processing chamber and a filtering device; a network of input and output lines operatively coupled to one or more of a source chamber, buffer chamber, waste chamber and collection chamber, and a controller that controls a mass of the processing chamber at a desired value based on an influx and a permeate flux of the processing loop.

DRAWINGS

These and other features, aspects, and advantages of the present invention will become better understood when the following detailed description is read with reference to the accompanying drawings in which like characters represent like parts throughout the drawings, wherein:

FIG. 2 is a flow chart for an example of a multi-step process flow of cell harvesting method of the invention.

These and other features, aspects, and advantages of the present invention will become better understood when the following detailed description is read with reference to the accompanying drawings in which like characters represent like parts throughout the drawings, wherein:

DETAILED DESCRIPTION

Figure 1:
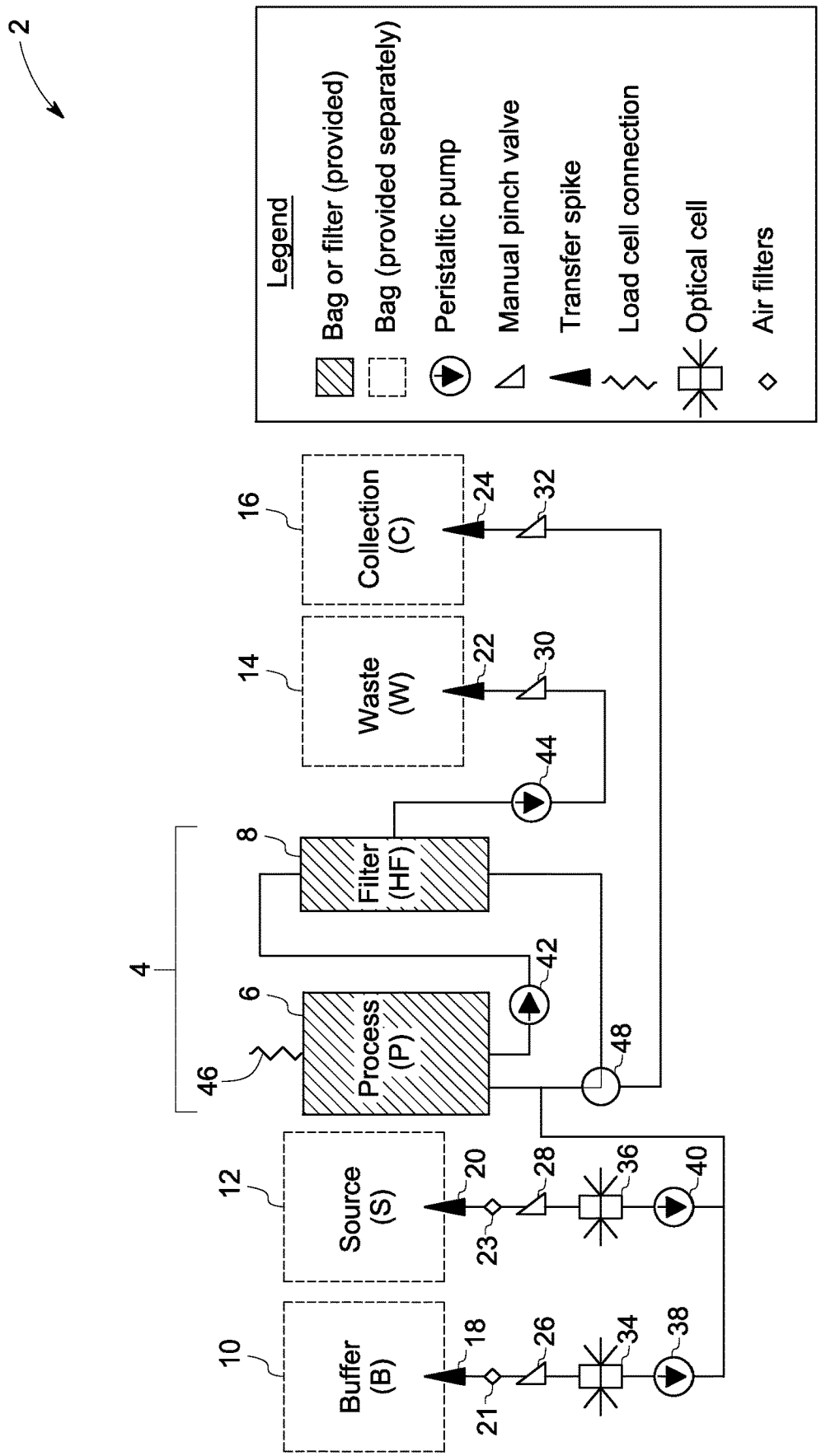
FIG. 1 is a schematic architecture of an embodiment of a cell harvesting device and associated method of operating a disposable unit of the invention.

One or more examples of the methods for harvesting cells from various sources are provided, wherein at least one of the methods comprises repeated washing and concentration steps. One or more embodiments of a device for processing or harvesting cells are also provided. A control law is another aspect of one or more of the methods, which keeps a desired mass of the processing chamber constant. The methods enable the process to be independent of the initial cell sample volume.

To more clearly and concisely describe and point out the subject matter of the claimed invention, the following definitions are provided for specific terms, which are used in the following description and the appended claims. Throughout the specification, use of specific terms should be considered as non-limiting examples.

As used herein, the term "chamber" refers to any object capable of containing a fluid within its confines for at least a temporary period of time having at least one port for materials to enter or exit the chamber. Some of the non-limiting examples of the chambers are processing chamber, buffer chamber, source chamber, or collection chamber.

As used herein, the term "processing material" refers to a material, which helps to process the cells during one or more of the processing. Non-limiting examples of the processing material include buffer, media, or water.

As used herein, the term "influx" refers to the mass or volume flow rate of material entering the processing loop comprising the processing chamber. The material may be a processing material such as, but not limited to, buffer, media, or a source material comprising cells.

As used herein, the term "permeate flux" refers to the mass or volume flow rate of the material that passes through the pores of the filter membrane. For example, in a typical hollow fiber microfiltration system, the volume of fluid sent to the filter is referred to as filter feed flow, the fluid that flows through the center of the fiber is the retentate and the fluid flow rate that permeates through the membrane wall of the hollow fiber filtering device, is known as "permeate flux". The term "permeate flux" is interchangeably used herein as "waste flux".

The term "operatively coupled" refers to a connection, wherein the connection may be through, but is not limited to, one or more lines or tubing. For example, the filtering device, one or more chambers or the network of input and output lines may be coupled to the source pump or the permeate pump via one or more lines or tubing. In some embodiments, a network of input and output lines is operatively coupled to one or more of the source chamber, buffer chamber, waste chamber and collection chamber. The network of lines or tubing is coupled to one or more chambers to complete the process of harvesting cells.

The term "setpoint" refers to a value of a desired volume or desired mass of a chamber, which is settable at the time of the cell harvesting process. The setpoint may be different for various steps of the cell harvesting process. For example, the setpoint of a processing chamber may be different for a loading step, washing step, or concentrating step. The setpoint determines the direction of the fluid flow to the processing chamber, and/or regulate the procedure depending on the process requirement.

In one example of the method of harvesting cells from a fluidic material in a processing loop, which comprises a processing chamber and a filtering device, wherein the fluidic material has a volume and the processing chamber has an overall capacity, the method comprises, circulating the fluidic material through the processing loop and balancing an influx of the fluidic material into the processing chamber with a permeate flux of the filtering device to maintain the volume of the fluidic material in the processing chamber at a constant value, concentrating the cells by increasing the permeate flux of the filtering device relative to the influx of the fluidic material into the processing chamber; and collecting the concentrated cells in a collection chamber.

As noted, in this example, the fluidic material is circulated through the processing loop by balancing an influx of the fluidic material with the permeate flux of the filtering device to maintain the volume of the fluidic material in the processing chamber at a constant value. In this step, the fluidic material may be passed through the processing chamber, and the processed fluidic material is then passed through the filtering device. The permeate flux of the filtering device is disposed to the waste chamber, and the retentate may further enter the processing loop and pass through the processing chamber again, followed by a pass through the filtering device. The fluidic material may be circulated through the processing loop repeatedly depending on the application requirement or user need. In some examples, the circulating step leads to concentration of the fluidic material, and more specifically to concentration of the source material. As the circulating step includes filtering, the impurities present in the cell sample may be removed by employing this step.

As noted, the cells may be concentrated by increasing the permeate flux of the filtering device relative to the influx of the fluidic material into the processing chamber. If the total volume of the fluidic material that is introduced into the processing loop is equal to or greater than the overall capacity of the processing chamber, then concentration of the fluidic material is required. In some examples, when the volume of the source material is greater than the overall capacity of the processing chamber, the source material is subjected to a concentration step. In this step, excess buffer or media along with any impurities present in the source material is removed from the source material and the cells are getting concentrated. The concentration of cells may be customized depending on the application requirement or user need.

As noted, the cells are collected in a collection chamber after concentrating the cells. As mentioned earlier, the impurities are significantly reduced in the concentrated cells, such as DMSO or glycerol which may be used for cryopreservation. At this point in the process, the cells are now in a minimal volume of media or buffer. The washed concentrated cells after the harvesting procedure may directly be used for any cell-based application.

In one or more examples, the fluidic material comprises a source material, a processing material or a combination thereof. Each of the source material and the processing material has a total volume. The combination of total volume of the source material and the processing material is the total volume of the fluidic material. The processing material is selected from a liquid media, a buffer, or a combination thereof. The source material may comprise cells in a liquid media, buffer or combinations thereof. As noted, the processing material typically comprises at least one of a media or buffer, and for the entire procedure, the media used is a liquid media, and the buffer used is a buffer solution. The processing material is mainly used for washing of the cells while passing through the processing loop. In some examples, the processing material may be introduced into the processing chamber via an inlet port. The processing material may be delivered to the chamber automatically. The source material is typically stored in a chamber during the method of cell harvesting, and is called a source chamber. A chamber that typically stores processing material at the time of the cell harvesting procedure and is called a buffer chamber.

One example of the method of harvesting cells, further comprises loading the total volume of the source material to the processing loop, wherein the total volume of the source material is less than or equal to the overall capacity of the processing chamber. In one specific example, the total volume of the source material may be equal to the overall capacity of the processing chamber, wherein the total volume of the source material is transferred from the source chamber to the processing chamber. In another example, the total volume of the source material may be less than the overall capacity of the processing chamber, wherein the total volume of the source material is transferred from the source chamber to the processing chamber, and the process is known as loading, more specifically, complete loading of the source material. In this example, the total volume of the source material is pumped into the processing chamber. In some examples, the source material is first poured into a source chamber, wherein the source chamber typically stores the source material during the harvesting procedure. The source material is then loaded to the processing loop via an inlet port.

In some examples of the method, the processing chamber has a desired volume. The desired volume of the processing chamber is typically less than or equal to the overall capacity of the processing chamber. In one example, when the total volume of the source material is greater than the desired volume of the processing chamber, the method further comprises concentrating the source material. In this example, the source material is transferred to the processing chamber in a continuous process or an intermittent process. In one example, the desired volume of the processing chamber is equal to the overall capacity of the processing chamber. In this example, if the total volume of the source material is greater than the overall capacity (or desired volume) of the processing chamber, then a fraction of the total volume of the source material is transferred to the processing chamber, and the process may be an intermittent loading of the source material. In the same example, the process of loading may be continuous while the source material is transferred to the processing loop, and the process follows continuous processing and concentrating steps. In this case, the transferred volume of the source material to the processing loop is controlled as the transferred volume is less than the desired volume of the processing chamber. Controlling a flow rate of the loading of the source material may accomplish this condition. In this example, the source material may be concentrated simultaneously at the time of loading.

One example of the method of harvesting cells, further comprises washing the cells by introducing the processing material into the processing loop and balancing an influx of the processing material with the permeate flux of the filtering device to maintain the volume of the fluidic material present in the processing chamber at a constant value. The cells may be washed by repeated influx of the processing material in a continuous way and/or balancing the influx of the processing material with the permeate flux of the filtering device to maintain the volume of the fluidic material present in the processing chamber at the constant value.

For diluting the impurities present in the source material, the processing material is pumped into the processing chamber and then to the filtering device. In this step, the source material and processing material are further circulated through the processing loop. The source material is repeatedly passed through the same path, while the processing material is simultaneously introduced to the processing loop. The buffer solution or media is introduced to the processing loop for washing the cells or diluting the source material and removing various impurities by filtering the fluid. The source material and processing material typically pass through the filtering device for filtering out unwanted impurities present in the sample and excess processing material to purify the cells before use. In some examples, the media comprising the cells may comprise a preservative solution, e g. DMSO or glycerol, and the media may be diluted with a buffer solution or liquid media, which may not contain any such preservative. For example, the removal of residual impurities reduces the concentration of soluble additives present in the cryogenically-preserved source material, such as DMSO. In some applications it is desirable to reduce the concentration of DMSO in excess of 100× dilution prior to use. During the filtration procedure, the filter permeate passes through a permeate pump and enters into a waste line thereby extracting excess media or residual impurities from the source material, and processing material passes through the filter.

In some examples, the cells are concentrated by increasing the permeate flux of the filtering device relative to the influx of the processing materials and the source material into the processing chamber. In these examples, the permeate flux may be increased by controlling the processing material flow. In one example, (a) the influx of the processing materials may be set to zero, so that the cells are only concentrated in this step. In another example, (b) the influx of the processing materials may be set to a value less than the permeate rate, so that the step may be a combination of concentration and washing of the cells. In this example, a desired volume of the fluidic material in the processing chamber is referred to herein as a setpoint. Depending on the process requirement, the setpoint may be varied in various conditions. For example (b), a steady change of a setpoint is required. In this example, the influx of the buffer rate is set at a fraction of the permeate rate using the control law. The cells may further be concentrated by passing through the processing loop repeatedly, and then the concentrated cells are collected in a collection chamber.

In some examples, the method of harvesting cells comprises introducing a processing material into the processing loop to rinse the processing loop before or after introducing the source material, or in gradual or alternating steps. In some examples, the processing material is introduced to the source chamber to rinse the chamber after transferring the total volume of the source material to the processing loop, and the rinse volume of the processing material is transferred to the processing loop. In one or more examples, after rinsing the processing loop, the source material is pumped into the processing loop, and passed through the processing chamber followed by passing through the filtering device. The source material is then circulated through the processing chamber and the filtering device, keeping the volume of the fluidic material present in the processing chamber constant.

The processing loop may operatively be coupled to the source chamber and the buffer chamber. The connections to the source chamber and the buffer chamber comprise optical sensors to determine the presence of liquid in the tubing. The method further comprises introducing sterile air directly or indirectly to the source chamber, buffer chamber or combination of both. In one example, the sterile air is introduced directly to the source chamber, buffer chamber or both. The sterile air may also be introduced indirectly, wherein the sterile air is introduced to the chambers via one or more connecting tubes, adapter, or any other connecting means.

The fluidic material used for harvesting cells may be different in different cases. When two different fluidic materials are used for two different cases having the same density, typically a definite volume of each of the fluidic materials has the same mass. In an alternate embodiment, when the two fluidic materials have different densities, same volumes of each of the fluidic materials have different mass. In this embodiment, the method generally considers the total mass of the source material, processing material, or fluidic material present in the processing chamber instead of total volume.

One example of a method of harvesting cells from a fluidic material in a processing loop, which comprises a processing chamber and a filtering device, wherein the fluidic material has a mass and the processing chamber has an overall capacity, the method comprises, circulating the fluidic material through the processing loop and balancing an influx of the fluidic material into the processing chamber with a permeate flux of the filtering device to maintain the mass of the fluidic material in the processing chamber at a constant value; concentrating the cells by increasing the permeate flux of the filtering device relative to the influx of the fluidic material into the processing chamber; and collecting the concentrated cells in a collection chamber. The method further comprises loading the total mass of the source material to the processing loop prior to circulating the fluidic material, wherein the total mass of the source material is less than or equal to the overall capacity of the processing chamber.

As noted, the processing chamber has a desired mass that is less than or equal to the overall capacity of the processing chamber. The method further comprises concentrating the source material, wherein the mass of the source material is greater than the desired mass of the processing chamber. The method further comprises washing the cells by introducing the processing material and balancing an influx of the processing material with the permeate flux of the filtering device to maintain the mass of the fluidic material in the processing chamber at a constant value.

The method of harvesting cells using, for example, device architecture 2, as illustrated in FIG. 1, is capable of servicing a wide range of sample volumes with minimal impact of the requirements of associated hardware such as pumps, valve actuators, or sensors. One or more peristaltic pumps are utilized in the system to prevent movement of fluid or air in the network of input and output lines. It eliminates the need for additional clamps to prevent fluid flow. As noted, the disposable is composed of a central processing loop 4 (FIG. 1) and a network of input/output lines, and the processing loop comprises a processing chamber 6 and a hollow fiber filter 8. During the cell harvesting procedure, cells are collected and re-circulated in the process loop 4. The input and output tube network is terminated with one or more connection means. In some embodiments, the connection means may include but is not limited to transfer spikes, luer connections, or sterile tubing welding. In one embodiment, the connection means may be transfer spikes. In some embodiments, the input and output tube network is terminated with transfer spikes for connection to buffer 18, source 20, waste 22 and collection bags 24, which may be disposable and sold separately. The reason for this separation of the input (buffer 10 and source 12) and the output bags (waste 14, and collection 16) from the central disposable cartridge that enable the system to process a wide range of anticipated samples and process conditions, such as volume of the sample, or residual reduction factors. The buffer bag 10 and source bag 12 are connected to the sections of tubing that interface with optical sensors 34 and 36 respectively to determine the presence of liquid in the lines.

Manual pinch valves are present on the tubing after the transfer spikes. Fluid sensors 34 and 36 are present after the manual pinch valves 26 and 28 on the buffer and source tubes. In some embodiments, the fluid sensors are optical sensors. The pumps 38, 40 and 44 may comprise the function of pinch valves 26, 28, and 30 respectively. For introducing sterile air to the tube set, the source and buffer tubes may comprise optional valves with air filters 21 and 23 in the FIG. 1. In some embodiments, the waste and collection tubes may comprise manual pinch valves of 30 and 32 respectively.

In non-limiting examples, the components for the introduction of sterile air may be a tee fitting with a one-way valve (21, 23) terminated by a 0.22 µm air filter. The air introduction mechanism ensures that in the absence of air in the source or buffer bags, the associated tubes are still filled with air, signifying the emptying of the associated bags through the detection of the air with the fluid sensors. The input and output lines may have a manual pinch valve to control flow during installation and removal from the hardware system. The manual pinch valves allow the operator to connect the disposable kit to the external bags and prevent any unwanted fluid flow. Without manual pinch valves, if the kit is connected to the bags prior to insertion into the device, the fluid may flow based on gravity or pressure. Only once the kit is inserted and the doors are closed would fluid flow stop because the pumps act like check valves. Thus, manual pinch valves are desirable if the operator connects the disposable kit prior to insertion of the kit and door closure of the hardware system.

As illustrated in FIG. 1, the disposable contains one turn valve 48 to control the direction of flow in the processing loop. The turn valve 48 is repositioned to empty the processing loop. Upon installation of the disposable unit into the hardware system, the peristaltic pumps 38, 40, 42 and 44 are engaged with the disposable tubing at four locations, the fluid sensors 34 and 36 are engaged with the source and buffer tubing, the filter unit 8 is engaged with the hardware system, the processing chamber 6 is attached to the load cell sensor 46, and the turn valve 48 is engaged with an actuator (motor), as shown in FIG. 1. Silicone tubing may be used near or at the pump locations to provide enhanced robustness and flow rate accuracy. When the peristaltic pumps are engaged and stationary, the pump rotors prevent fluid flow. Upon pump engagement the manual pinch valves may be opened without altering the position of liquids in the system. A single load cell 46 (as showed in FIG. 1) is used to monitor the mass of processing chamber for a wide range of sample volumes. The architecture used for the process of harvesting cells as illustrated in FIG. 1 is independent of sample volume.

An exemplary embodiment of the method of harvesting cells is described by the flow chart, as illustrated in FIG. 2. One or more steps of the depicted flow chart may be eliminated in some examples, or one or more steps may be added to the existing flow chart in some examples of the methods, depending on the process requirement or user need. Before the process begins, all of the chambers, processing loop, network of input and output lines or ports are connected to each other to form a complete unit and are enclosed in a hardware system as shown in FIG. 2, step 1. One or more pinch valves are attached to each of the lines, or at the end of each of the chambers to control the flow of liquid at the time of the cell-processing or before starting the process. When the process starts, the pinch valves are released to allow the fluid flow. To rinse the system before processing, the processing materials (buffer or media) may be passed through the processing loop and may be discarded into the waste chamber, as illustrated in FIG. 2, step 2. The cell sample is loaded on to the source chamber and directed to the processing loop, as shown in FIG. 2, step 3. The fluid is repeatedly passed through the same path of the processing loop with the influx and permeate being balanced, until the entire cell-sample volume is loaded.

In some examples, after the initial emptying of the source chamber, the processing material is introduced into the source chamber to rinse the chamber, though rinsing of the source chamber is optional. Processing material is transferred to the source chamber through the coordination of the source and buffer pump rates and directions of flow. To ensure that only the processing material is pumped into the source chamber, the buffer pump rate is set to be equivalent or greater than the source pump rate. Additionally, the connection of the source pump to the processing loop occurs between the buffer connection and the processing loop. In this way, the need for an additional turn valve to control the flow is unnecessary. After rinsing of the source chamber, the buffer passes through the same pathway to repeat the cycle, as shown in FIG. 2, steps 4a-b.

In some examples, it is desirable to reduce the volume of the processing material and the source material prior to washing (dilution step), and thereby potentially reducing the time required to achieve a desired level of residual reduction. The volume of the processing material is reduced and the source material is concentrated by repeated filtration (as shown in flow chart of FIG. 2, step 5). In accordance with some embodiments, the method of concentrating cells comprises the step of balancing an influx of the processing material into the processing chamber with a permeate flux of the filtering device to maintain the mass of the processing chamber at a constant value. In this example of the method, the processing chamber has a mass, and the mass of the processing chamber is kept constant during entire process. The desired mass of the processing chamber may be kept constant by balancing a mass of the incoming fluid (or influx of the processing material) to the processing loop with a mass of the outgoing fluid (a permeate flux of the filtering device) from the processing loop.

After concentration, the cells are washed repeatedly by diluting with the processing material (FIG. 2, step 6). To maintain the mass of the processing chamber at a constant value, an influx of the processing material into the processing loop is balanced with the permeate flux of the filtering device by controlling the volume of the fluid in the processing chamber. Following the washing step, the source material may be concentrated by repeated filtration by removing the excess processing material (FIG. 2, step 7). The cells are harvested from the media followed by collection in a collection chamber (FIG. 2, steps 8). In some examples, the processing loop comprising the processing chamber is then rinsed by introducing an additional processing material, and then this rinsed material is collected in the collection chamber (FIG. 2, steps 9a, 9b). The loading and washing steps of the cell harvesting procedure employ regulating the mass of the processing chamber to various setpoints (desired mass of the processing chamber) by controlling the fluid-flow into (source and/or buffer pump rates) and out of (waste pump rate) the processing loop.

During loading of the sample in this example, the mass of the liquid in the processing chamber is controlled to a setpoint, known as a first setpoint. The first setpoint is a mass of the processing chamber. In one example, the first setpoint is assumed to be SP1. The fluid material loss due to the filter permeate flux is compensated by introducing incoming processing material from the buffer chamber, or the source material from the source chamber. In this example, if the first setpoint "SP1", is greater than the mass of the fluid (comprising cells and/or buffer or media, i.e., from a previous rinsing or loading step) present in the processing chamber, and the estimated mass of fluid in the source chamber, say "$m_p$", therefore in this case, SP1>$m_p$. In this example, the entire fluid present in the source chamber may be transferred to the processing chamber without concentrating the cells. If the entire amount of the source material (present in source chamber) is transferred to the processing chamber, then the mass of the existing fluid in the processing chamber (e.g., the fluid used for rinsing) and the estimated mass of the source material must be less than or equal to the setpoint. This process continues until the source chamber is emptied and the mass of the process chamber is still less than or equal to the first setpoint. The process of transferring fluid from the source chamber to the processing loop is completed when the optical sensor installed on the line operatively connected to the source chamber detects the presence of air in the line.

In another example, SP1 may be less than the sum of the mass of the starting mass of the fluid in the processing chamber and the estimated mass of the source material of the source chamber. In this particular example, the source material from the source chamber may be added directly to the processing loop until the mass of the fluid in the processing chamber is equal to SP1. The remaining source material in the source chamber and the fluid in the processing chamber must be concentrated. The remaining source material is also loaded and the mass of the processing chamber is simultaneously maintained at SP1. The cells are then concentrated by the repeated filtration, wherein the influx of the source material from the source chamber is balanced with a permeate flux of the filtering device to maintain the mass of the processing chamber at SP1.

In this example, the source chamber is rinsed with a desired amount of buffer solution. If the mass of the processing chamber $m_p$ is less than the first setpoint SP1, and the mass of the rinsed (buffer) solution present in the source chamber is less than the difference between SP1 and $m_p$, the entire buffer solution or media used for rinsing the source chamber is transferred to the processing chamber without concentrating the cells. The rinse step may be repeated multiple times. In the example where the mass of the processing chamber $m_p$ is equal to SP1, the source material in the processing loop typically must be filtered repeatedly, again balancing the influx of the rinse material in the source chamber with the permeate flux.

In one example, when the source chamber is cleaned and emptied, the mass of the fluid in the processing chamber may be further reduced to another setpoint, called "second setpoint", wherein the second setpoint is a reduced mass of the process chamber, for example if the second setpoint is assumed to be SP2, then SP2<SP1. To reduce the mass of the processing chamber from SP1 to SP2, the fluid material in the process loop is reduced through repeated filtration wherein the fluid flows from the processing chamber, through the filter, returning to the processing chamber. No additional material (buffer or source) is added during this volume adjustment procedure.

The procedure of introducing buffer or media to the processing loop and circulating through the processing chamber and the filtering device enables the wash procedure.

During this step, the filter permeate flux is matched with the flow of incoming media or buffer from the buffer chamber. This new media or buffer dilutes the soluble residuals in the source material. The overall reduction of residuals present in the source material is determined by an operator, for example 100×.

Once the washing procedure is completed, the volume of the processing material in the process loop may be reduced to its minimum volume to a new setpoint, known as "third setpoint" SP3. In this example, the conditions of all three setpoints during the entire method are SP3<SP2<SP1. Similar to the mass reduction from SP1 to SP2, the fluid material in the process loop is reduced through repeated filtration wherein the fluid flows from the processing chamber through the filter and returning to the processing chamber. No additional material (buffer or source) is added during this volume adjustment procedure.

The step of transferring the processing material and the source material to the collection chamber commences with actuation of a turn valve to redirect the processing material from the processing loop to the collection chamber. The processing loop pump 42 in FIG. 1 is used to pump fluid from the processing chamber, through the filter to turn valve 48 and into the collection chamber. To prevent additional filtering during the collection step, permeate pump 44 may be stopped. Once the process loop is empty, the turn valve actuates to isolate the collection chamber. The processing loop may be rinsed with the processing material, such as buffer or media. This rinse volume is either directly collected or may be concentrated prior to an additional collection step. The processing loop and the network of input and output lines may be housed in a hardware system, which is a closed chamber having one or more doors. One or more of the source chambers, buffer chambers, waste chambers and collection chambers may be present adjacent to the hardware system. Manual clamps are attached to the source chambers, buffer chambers, waste chambers and collection chambers prior to opening the door of the hardware system to prevent any leakage or spillage of liquid from those chambers. The collection chamber is then separated from the remainder of the disposable, and the washed and concentrated cells from the collection chamber are saved and preserved for further use. The excess media, unwanted particles and/or impurities from the source material drain out and are disposed into the waste chamber after passing through the processing loop. In one example, the disposable comprising the processing loop, and the network of input and output lines is discarded after the procedure.

One of the methods for controlling mass of the processing chamber of the cell harvesting device comprises, creating an estimator for a flow rate of the permeate pump using velocity of the source pump or buffer pump, a calibration constant of the source pump or buffer pump, and the rate of change of the mass of the processing chamber. The method further comprises setting a flow rate through the source or buffer pump using a control law comprising the estimator and a feedback term. The feedback term comprises the rate of change of the mass of the processing chamber, a setpoint and a feedback gain, and wherein the feedback gain is greater than zero and the mass of the processing chamber is constant at the setpoint. In this example, the harvesting device comprises a filtering device, the processing chamber, a network of input and output lines operatively coupled to a source pump, a buffer pump and a permeate pump.

Figure 3:
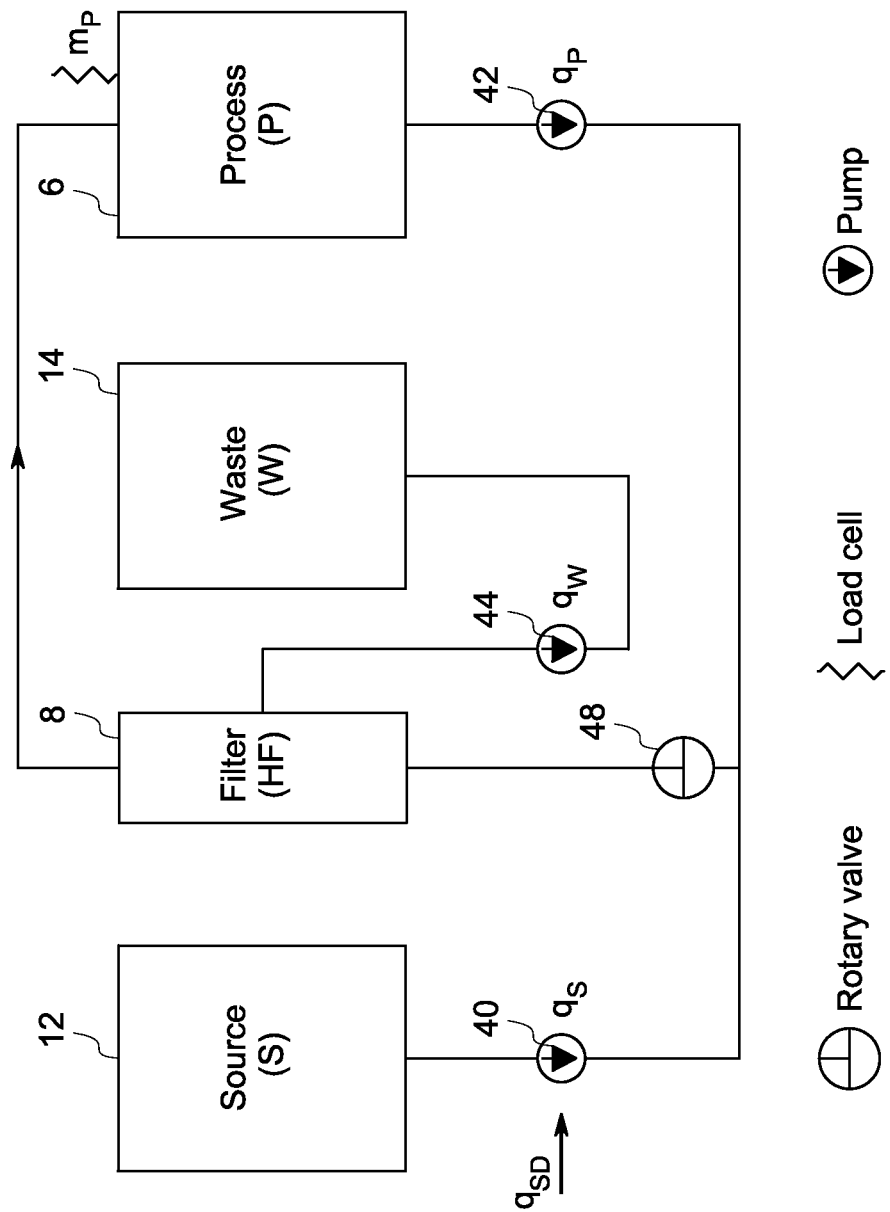
FIG. 3 is a schematic drawing for an example of a mass-flow diagram of the invention for processing cells.

A mass flow analysis of the system depicted in FIG. 3 shows that in order to hold the mass of the processing chamber constant, the mass flow rate through the source pump, $q_s(t)$, has to equal the mass flow rate of the waste pump, $q_w(t)$, wherein an equation may be represented as:

$$q_s(t) = q_w(t), \forall t \tag{1}$$

However, this simple implementation is complicated by the fact that the potential filter clogging and other phenomena that impact permeate flux of the filter results in a change of permeate pump flow rate with time, even when the waste pump velocity is fixed. Hence, the waste pump flow rate may not be easily calculated using the velocity. In some embodiments, the pump velocity may be a linear velocity or may be a rotational velocity. A wide range of source volumes implies a wide range of waste volumes, making it impractical to directly measure the mass of the source and waste chambers. Moreover, the instantaneous source pump flow rate $q_s(t)$ may not be exactly controlled; instead the desired flow rate may be set.

To overcome these limitations, the mass of the processing chamber is balanced by creating an estimator, $q_{We}(t)$, for estimating correctly the waste pump flow rate using the source pump velocity $\omega_s(t)$, a source pump calibration constant $\gamma$, and the processing chamber flux $dm_p(t)/dt$, which are all known constants or measured variables. The estimated waste flux is given by $$q_{We}(t) = \gamma \omega_s(t) - \frac{dm_p(t)}{dt} \tag{2}$$

Alternative embodiments of the estimator (Eq 2) comprise estimating the waste flux, $q_{We}(t)$, using a waste pump calibration constant $\beta$ multiplied by the waste pump velocity $\omega_W(t)$, such that $$q_{We}(t) = \beta \omega_W(t) \tag{2.1}$$

or by using the commanded waste pump flux, $q_{We}(t) = q_{Wd}$.

A desired instantaneous flow rate is set through the source pump, $q_{Sd}(t)$, using the control law:

$$q_{Sd}(t) = q_{We}(t) - k\{m_p(t) - m_{pd}\} \tag{3}$$

where $m_{pd}$ is the setpoint at which the mass of the processing chamber is to be held and $k > 0$ is an arbitrary user-settable feedback-gain. In addition to the feed-forward estimate, $q_{We}(t)$, of the permeate flux, the control law includes a feedback term, $-k(m_p(t) - m_{pd})$. The feedback term is important to proper operation of the automated system because in real-time, the feedback term accounts and adjusts for errors introduced by system and model inaccuracies such as but not limited to, the estimate of the permeate flux not exactly matching the actual permeate flux, the source pump flux not exactly tracking the desired pump flux (pump following error), calibration inaccuracies, electrical and mechanical noise in the system, and other disturbances. Furthermore, the waste flux estimate from equation 2.1 may also be set to a constant value, including zero. However, with these alternative embodiments (from equation 2.1) substituted into Eq. 3, the mass tracking errors in the steady state process should not be made arbitrarily small with a large enough gain k.

When the controller acts on the system, the mass tracking errors in the steady state process may be given by:

$$\lim sup \|m_p(t) - m_{pd}\| \leq \lim sup \frac{1}{k} \|e(t)\| \tag{4}$$

That is, the effect of all the errors, e (t), in the system and the model may be made arbitrarily small by choosing the feedback gain k which is large enough to minimize the error to an acceptable level. In practice, the effect of the errors may be substantially reduced, but the maximum value of k and thus the maximum reduction of errors in the setpoint is limited due to non-ideal behaviors such as, but not limited to, actuator drive saturation and sensor noise.

An example of the cell harvesting device comprises a processing loop which comprises a processing chamber and a filtering device; a network of input and output lines operatively coupled to one or more of a source chamber, buffer chamber, waste chamber and collection chamber, and a controller that controls a mass of the processing chamber at a desired value based on an influx and a permeate flux of the processing loop.

The processing loop comprises the processing chamber and a filtering device, which may be a part of a disposable unit. The disposable unit may comprise the processing loop and a network of input and/or output lines (interchangeably used herein as "inlet and/or outlet ports"). In one or more examples, the disposable unit may be single use. In some other embodiments, the processing loop and the network of inlet and/or outlet ports as a whole forms a re-usable unit, which may be used multiple times. The processing loop comprises a direction controlling valve to control a direction of fluid-flow in the processing loop. In some embodiments the direction controlling valve may comprise a turn valve, rotating valve, stop cock or combinations thereof.

The cell harvesting device comprises a processing chamber, and one or more additional chambers for various steps. One or more chambers used for the cell harvesting procedure may be a flexible or a rigid container. In one or more examples, the chamber is a cylinder, bottle, flask, tank, bag or combinations thereof. For example, the processing chamber may be a processing bag or tank. The chamber may be sealed via a stopper, lid, or other means, or may be constructed without a sealable opening. The chamber may be made of, for example, polymer or glass. One or more of the chambers comprise, but are not limited to processing chambers, buffer chambers, source chambers, waste chambers and collection chambers. One or more additional chambers may also be used depending on the process requirement and user need. The processing chamber comprises one or more inlet and/or outlet ports connecting to a network of tubes or lines operatively coupled to one or more additional chambers or to one or more pumps. For example, the inlet and/or outlet ports are connected to the filtering device, source chamber, buffer chamber or collection chamber.

Figure 4:
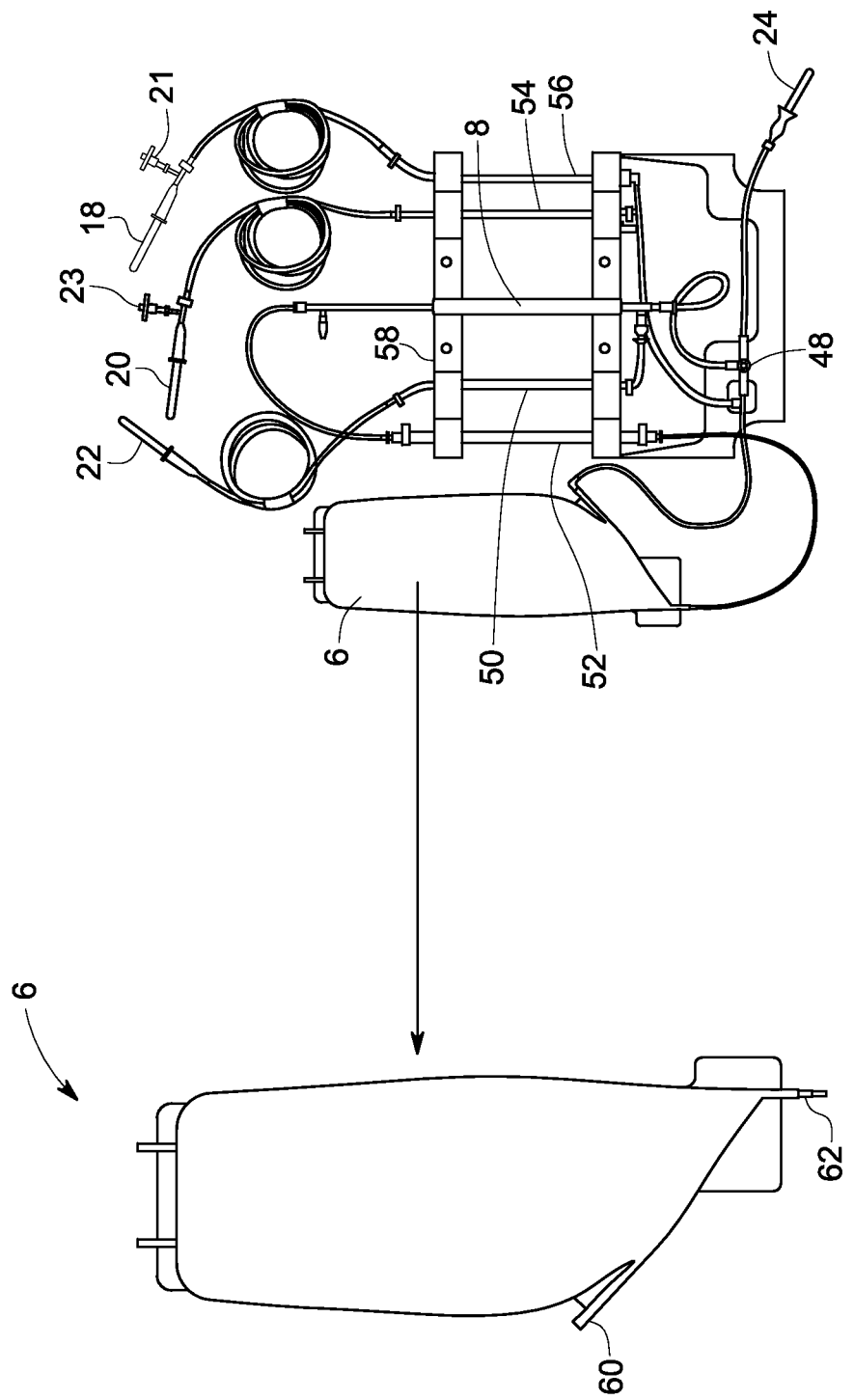
FIG. 4 is an image of an example of a disposable prototype of the invention for processing cells for low sample volume.
Figure 5:
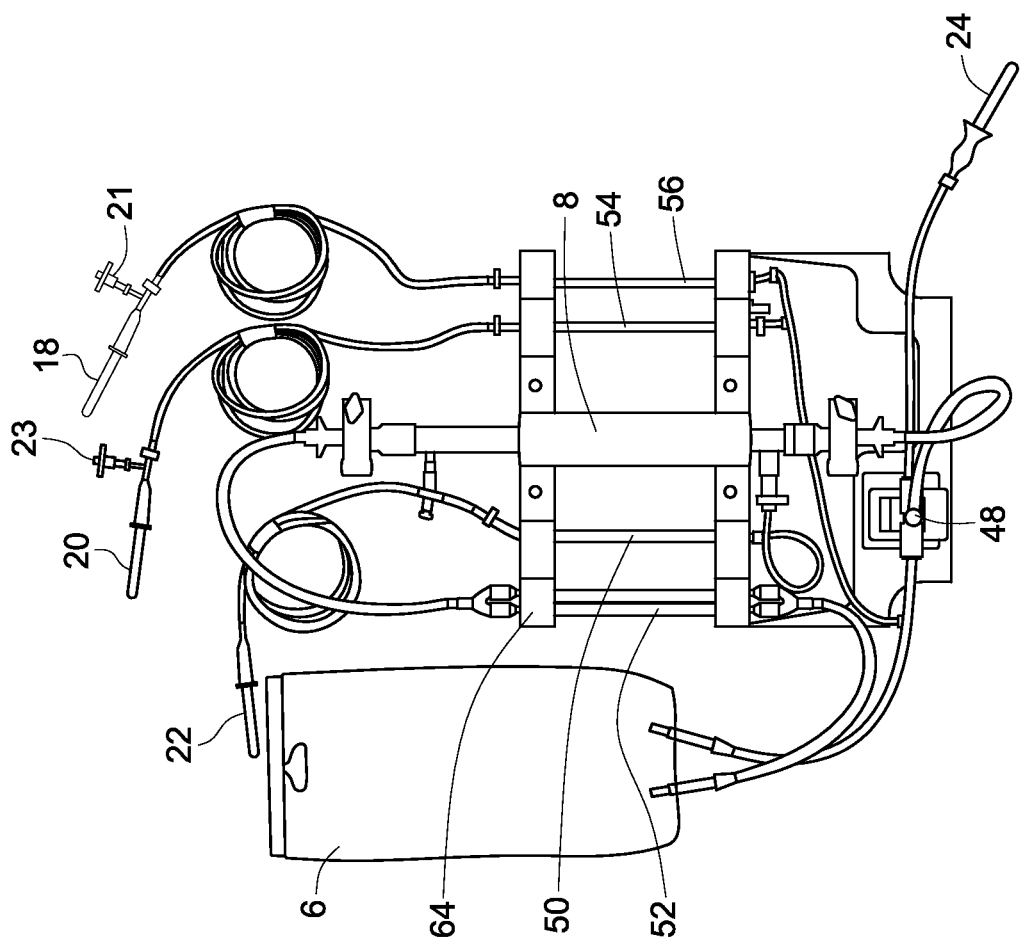
FIG. 5 is an image of an example of a disposable prototype of the invention for processing cells for higher sample volume.

In one or more examples, the processing chamber is independent of the initial sample volume of source material. The processing chamber volume does not need to scale with initial sample volume due to the novel control logic of the invention. The geometry of the processing chamber may minimize the hold-up volume for the small sample size but also support larger inlet and/or outlet ports for the large sample size. A single load cell with high sensitivity over a small range (of approximately 0-2 kg) is used to monitor the mass of the processing chamber for a wide range of samples (0.1-50.0 L). FIGS. 4 and 5 also show different process chambers in the form of fluid bags for the two different sample size configurations. The bag geometry may be the same for both the small and large sample volume disposable. FIG. 4 shows the low sample volume processing chamber 6 currently used with an advanced prototype. This bag has a conical sharp outlet 62 that is intended to maximize the recovery of cells from this portion of the disposable. Additionally bag 6 may be blow molded to eliminate seams that could result in additional sources of cell loss. For the bag shown in FIG. 4, the entry of the cells to the processing chamber through the elevated inlet port 60 and extraction of the cells out from the bag through the outlet port 62 positioned at the bottom of the conical section prevent sample loss for at least low sample volume.

The additional chambers, including a buffer chamber, source chamber, waste chamber and collection chamber, may have similar structure as the processing chamber. All of the chambers may be a sealed disposable component to contain of fluids during processing to preserve sterility. The "buffer chamber" is a chamber capable of holding processing material, e.g. buffer solution or liquid media. In some embodiments, the buffer chamber holds buffer solution, in some other embodiments, the buffer chamber may also hold liquid media independently. The buffer chamber may be a buffer fluid bag. The source chamber or buffer chamber may also comprise tubing interfaced with one or more fluid sensors, which may be optical sensors, to determine the presence of liquid in the tubing. The supply of buffer or media or source material may be determined by the response of the fluid sensor. The source chamber is similar to the buffer chamber that comprises cells suspended in a media. A flow of sterile air may be introduced into one or more tubes connected to the source chamber or the buffer chamber. The collection chamber holds the final product of concentrated cells after cell-harvesting. In one example, the processing chamber may be interfaced with Wave™ processing chambers (GE Healthcare).

One or more embodiments of the system may comprise a hollow fiber filter. The source material or processing materials introduced into the filter is known as input volume, the fluid or processing material coming out of the filter as retentate is known as output volume, and the fluid or processing material permeated or diffused out from the fiber wall is known as permeate. The filtering device and one or more tubing coupled to the filtering device are dependent of sample volume and processing flow rates. The hollow fiber filter is employed for separating cells from the media. In some embodiments, the hollow fiber filter has a pore diameter in a range from about 0.1 to 1 µm and an inner fiber diameter of 200 to 2000 µm and a fiber count of 4 to 400. In one example, the filter has pore sizes of 0.65 µm. Internal fiber diameter of the hollow fiber filter is typically in a range from about 200 to 2500 µm or 10 times the diameter of the biggest particles. In one example, the fibers have internal diameters of 750 µm. The thickness of the wall of the filtering device is in a range of about 20 to 200 µm.

In one or more embodiments, a controller is present that controls the mass of the processing chamber at a desired value based on an influx and a permeate flux of the processing loop. The device for harvesting cells comprises a system for data acquisition and system control. This module is connected to a series of custom interface boards for controlling the pump motors and valve actuator.

In one or more examples in which a wide range of sample volume requires the use of multiple disposables, such systems may have the overall architecture as shown in FIG. 1. In some embodiments, the network of input and output lines (or tubing or tube), and one or more of the chambers coupled to the lines are independent of sample volume. One or more peristaltic pumps are interfaced with the network of input and output lines. The input and output lines of the network may be terminated with transfer spikes, and the spikes are embedded in the input and output lines connecting to the source chamber, buffer chamber, waste chamber and collection chamber. The reason for separation of the input chambers from the disposable, such as source chamber or buffer chamber and output chambers such as waste chamber or collection chamber is due to the range of anticipated samples and process conditions, such as volume of various samples, or residual reduction factors. The source and buffer chambers may comprise sections of tubing that are interfaced with fluid sensors, which may be optical sensors, to determine the presence of liquid in the lines. In some embodiments, the input and output line is operatively coupled to one or more clamps to control a fluid-flow. In some embodiments, the processing loop comprises a turn valve to control the direction of fluid-flow in the loop. The geometry and material of these tube sections may be the same as the rest of these lines. However, assuming that the optical properties of the tubes may need to be able to identify the presence of liquid in the tubes.

The tubing and associated components for the source, buffer, waste and collection chambers or bags may be the same for all sample volumes. This commonality is enabled using the wide range of flow rates achieved with the peristaltic pumps present on the tubes or lines and also enabled by the filter while ensuring flow rates are in achievable ranges. However, the processing loop, including the filtering device and tubing, may be scaled up or down with the sample volume. The increase in tube diameter enables the fluid to pass with higher flow rates but results in higher hold-up volumes that impact the minimum output volume. The inner diameter of the valve and any other connections may scale with the sample volume as well to minimize the flow restrictions that result in shearing of the cells. During the procedure, the volume of fluid present in the processing chamber may be independent of the initial sample volume due to the implementation of a control law to regulate the whole process. The control law addresses the need to hold the mass of the processing chamber constant by balancing the filter's permeate flux with influx of the incoming fluid either from the source chamber or buffer chamber.

Upon installation of the disposable into the hardware system, peristaltic pumps are engaged in the disposable tubing, such as waste loop 50, feed pump loop 52 or loop from processing chamber, source pump loop 54, and buffer pump loop 56, at four locations as shown in FIG. 4 and FIG. 5. FIGS. 4 and 5 represent prototypes of disposables, which are designed for low sample volumes, such as ~1 L samples and high sample volumes, such as ~10 L samples, respectively. The disposables are independent of sample volume within a maximum range. For example, the processing chamber of FIG. 4, having an inlet 60 and an outlet 62, is independent of sample volume which is less than or equal to 1 L, and in another example, the disposable of FIG. 5 is independent of sample volume which is less than or equal to 10 L. The disposables shown in FIGS. 4 and 5 illustrate that the parts of the processing loop (6, 52, 8, 48) comprising the filter and tubing is scaled up or down with the sample volume. The pump tubes and filter unit are arranged in a co-linear orientation using a frame of assembly 58 (FIG. 4 or 5). This frame aligns the tubes with the peristaltic pumps and the turn valve 48 with the valve actuator during installation of the disposable unit. The advance prototype of FIG. 5 illustrates two lengths of tubes being used in the processing loop between the processing chamber and filter to achieve the high flow rates required for harvesting, wherein the frame of assembly for large volumes 64 is used.

The device is composed of several sub-systems including peristaltic pumps, turn valve actuators, a load cell for measuring the mass of the processing chamber, optical sensors, a system controller, and power suppliers.

One or more embodiments of the device comprise peristaltic pumps. Four pumps are independently controlled to direct flow. Source pump 40 directs flow to or from the source chamber 12 and from or to the processing loop; the buffer pump 38 directs flow to or from the buffer chamber 10 and from or to the process loop; the process loop pump or filter feed pump 42 directs flow from the processing chamber 6 to the filter 42; and the waste pump 44 directs fluid from the filter permeate to waste chamber 14 as shown in FIGS. 1 and 3. The pump motors, rotors and rollers are located on the main assembly. Upon closure and locking of the door, the correct tube compression is achieved between the pump shoe and pump rollers to ensure accurate pumping and reliable sealing of the tube when the pump is stopped. The width of the process loop pump rollers is larger than that of other channels in order to accommodate the use of two parallel pump lines needed to achieve the high flow rate of 3.0 L/min. A six-roller pump rotor with effective diameter of 64 mm may be used in the advanced prototype to limit the required engagement arc of the pump. Smaller roller diameters would necessitate the incorporation of larger tube sections in the disposable and thus increase the hold-up volume and potential for tube misalignment.

One embodiment of the device comprises one or more turn valve actuators. A single turn valve is used to alter the flow path direction from the process loop to the collection bag. A rotary actuator with a spring loaded engagement feature is designed to mate with the valve associated with multiple disposable sizes during installation of the disposable unit to the hardware system.

Some embodiments of the device comprise one or more load cells, depending on its requirement in the process. In at least one example, the load cell sensor is the primary means of process control. This sensor continuously monitors the mass of the processing chamber and enables the calculation of the filter permeate flux. In one example, the load cell sensor measures the mass of the processing chamber up to a mass of 2 kg.

Some embodiments of the device comprise one or more optical sensors, which may be used, for example as fluid sensors. Other type of sensors for a variety of measurement may also be used. In one embodiment, two optical sensors are positioned on the optically transparent source and buffer inlet tubes. These sensors measure the presence of liquid in these tubes and determine the status of the source and buffer bags. The presence of bubbles or a continuous stream of air results in a change of the output signal of the optical sensor. A threshold-based measurement is used to determine the status of these lines. For example, the sensor may provide a value which is more than the threshold value that is possible only in presence of liquid in the tubes, and thereby the sensor indicates the presence of liquid in the tube. In another example, the sensor may provide a value which is less than the threshold value in absence of liquid in the tubes, and thereby the sensor indicates that the absence of liquid in the tube. The optical sensors may also be used to detect the presence or absence of source or process material tubing and prevent the system to start if no tubing is present.

The device further comprises a power supply that may be an alternate current (AC) distribution system. The device may comprise multiple direct current (DC) power supplies, which may be required to operate the pump motors, valve actuator and control electronics. The electrical sub-system wiring scheme comprises an AC distribution panel, multi-level DC power connections to a custom interface board, flex cable signal connections between interface boards and system, sensors, switches, and indicator wiring to front panel interfaces and process pause and emergency stop buttons. Additionally, each modular drive is wired to an electric motor with a rotary encoder (either pump or turn valve). The back panel houses a standard electrical receptacle with a power switch, an Ethernet port for remote monitoring of the system and controller, and fans for component cooling.

Figure 6:
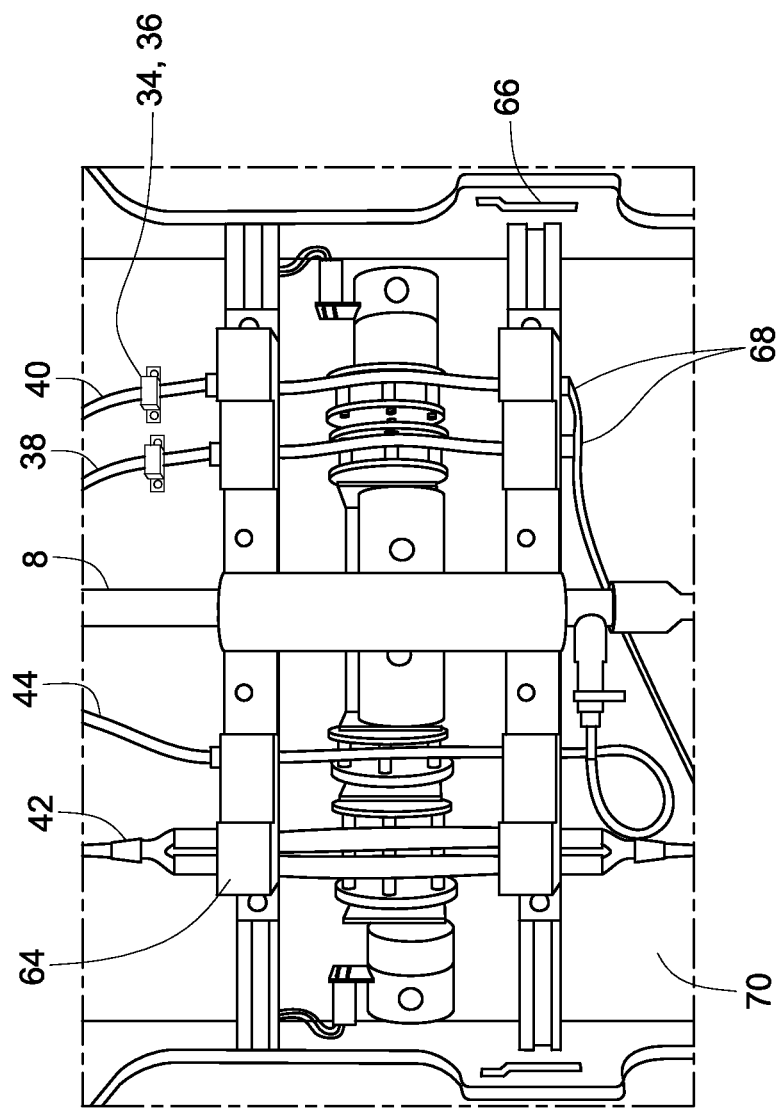
FIG. 6 is an image of an example of an interface of a hardware and disposable of the invention for processing cells for higher sample volume.

The disposable unit (or disposable kit) and one or more required chambers (such as processing chamber, source chamber, or buffer chamber) are housed in the hardware system. FIG. 6 illustrates the certain features of the interface between the disposable kit and the processing system. For device set-up, the user loads and the disposable into the processing system by inserting the frame 58 and aligning it with the guide pins. The frame ensures that the pump tubing sections are properly aligned with the pump rollers for each of the four pumps. Additionally, the guide pins locate and align the disposable turn-valve component with the turn-valve motor. Two switches engage with tabs on the disposable kit frame that enable the detection of the type of disposable kit 68 (i.e., small or large). The type of disposable kit 64, decoded by the software, may be defined appropriate ranges for the various input parameters (e.g., max processing flow rate). The doors of the hardware system are engaged by switches and a splash guard 70.

During insertion of the disposable kit, the user connects the buffer and source tubing to the buffer and source material supply chambers and the permeate and collection tubing to empty bags. In one embodiment, the connection of the tubing to the different bags may be facilitated by using transfer spikes supplied as part of the kit and connected to the tubing. The optical sensors are engaged with the buffer and source tubing. The optical sensors detect if the buffer and source tubes are present and then are used during the process to detect the presence of liquid or air in those tubes. Once the disposable kit frame is loaded, the user closes and locks the doors of the processing system. The quarter turn action of the door latch knobs engages each latch with a cam surface 66, wherein the cam surface refers to a surface that is inclined relative to the rotating tab on the quarter turn latches. The cam surface is cut into the support frame. The cam action aids in overcoming the tube compression forces as the door (and pump shoes) are locked into the closed position. The closed-and-locked position is detected using two switches (one for each of the door cam latches) that are activated when the door latches are in the fully locked position.

In addition to pump tubing engagement, the disposable kit frame also aligns the turn valve with the spring loaded engagement assembly that is driven by the turn valve motor. The spring loaded engagement assembly is designed to properly engage both the low-volume disposable kit stopcock and the high-volume ball valve. The engagement interface accommodates the dissimilar design in the high volume and low volume valve levers.

The operator may hang the processing chamber from the load cell. The software detects the presence of the processing chamber and prevents operation until the bag is properly located. The user may need to connect the tubing of the disposable kit to external bags (source, buffer, waste, and collection). During processing, the software typically rinses the buffer and source lines, as necessary, and detects if the bags are empty (through the detection of air in the line). Process state information is displayed on the front indicator panel. The "process state information" refers to the state of operation of the system, for example the state associated with when the system is ready for operation of harvesting cells may be indicated on the front panel. The operator may pause and resume the process using a push button switch on the indicator panel. LEDs are present in the system, to provide indication of the current process, for example, the LEDs may indicate the current process state of running, paused, or complete. In some embodiments, additional LEDs may also be present to illustrate the disposable kit size, door engaged state, or bag empty state. In some embodiments, the LEDs to check readiness of the process and fault in software may also be located on the front panel. The front panel also may include a low-level emergency stop button that disconnects power to the drives in the event of a serious electrical fault that is otherwise undetected by the software.

In one or more embodiments, the hardware system is configured for bench-top or cart-based operation with dimensions of no greater than 0.45 m, 0.47 m and 0.67 m for height, depth and width, respectively, with a volume of 0.14 $m^3$. The volume of the fluid processed per system may increase depending on the height of a solution tower or waste containers. The system may be designed to enable flexible operating conditions for research applications and a more restricted protocol for clinical applications.

Cell viability and activity may be influenced by the shear stress exerted on the cells during processing. The shear rates of $\leq 5000$ $s^{-1}$ have minimal impact on cell viability and activity. Shear rates are calculated based on the internal diameter of the hollow fiber lumen and the volumetric flow rate based on equation 5:

$$\gamma_{wall} = (32 \cdot Q)/(7 \cdot D^3) \qquad \text{Equation 5}$$

where, $\gamma_{wall}$ is the maximum shear rate, Q is the flow rate per fiber and D is the internal diameter of the fiber. Based on this equation a shear rate of 5,000 $s^{-1}$ is typically achieved with lumens having a diameter of 750 μm at a flow rate of 12.4 mL/min per fiber.

Depending on the user's desired overall residual reduction (dilution factor), the system computes the required amount of buffer necessary in the wash step, Step 6 (as shown in FIG. 2). However, during the prior and subsequent steps, the source material is diluted with buffer due to priming and rinse volume added to the system. Thus, the dilution factor for step 6 is in this example, dependent on the other steps in the process and may be computed real-time based on the user input parameters. Additionally, the dilution that occurs in the other steps is also, in this example, dependent on the overall volume and governing the required change in equations. Various steps of the cell processing method are illustrated in FIG. 2.

EXAMPLES

The cell harvester system may be used in both the transplantation and translational research and therapeutic applications. Although the sample sizes and compositions are dramatically different for these all limitations, the procedures are common. The following section details two non-limiting examples of cell harvesting method that comprises, 1) concentration and washing of a preserved cord blood sample and 2) concentration and washing of a high volume T-cell culture.

Example 1

Concentration and Washing of a Preserved Cord Blood Sample

A 25 mL sample of nucleated cord blood cells was washed using the cell harvester. The sample experienced a 100× reduction in preservative (DMSO) concentration and a 1× concentration factor to result in the re-suspension of cells in 25 mL of injectable media. This process is performed with a low volume disposable to minimize the potential cell loss associated with holdup volumes in the disposable kit. The low volume disposable supports the relatively low maximum process and permeate flow rates of 50 and 5 mL/min, respectively. The disposable was initially rinsed. Next, since the first setpoint (100 mL) exceeded the source volume (25 mL) the contents of the source bag were transferred to the processing chamber without concentration. The addition of cells to the priming volume diluted the DMSO by 2×. The source bag was then rinsed with two volumes of 25 mL that were directly transferred to the processing chamber, resulting in an additional 2× dilution factor. Steps 2 through 4 (as showed in FIG. 2) were performed quickly because of the high first setpoint relative to the transferred volumes. Step 5 concentrates the material in the process loop down to the second setpoint of 25 mL. This volume reduction was important to enable the rapid washing of cells. Step 6 provided an additional 10× dilution of the soluble additives in the concentrated cells. In step 7, the washed cells were concentrated to the final set-point of 10 mL and then transferred to the collection bag in step 8. In step 9, the process loop was rinsed twice, but the volume of rinsed material was reduced to 7.5 mL for each rinse prior to transfer to the collection bag in order to minimize the final volume. This rinse volume results in an additional 2.5× dilution in soluble residuals resulting in a total of 100× reduction. The total process time for this procedure was approximately 60 minutes.

Example 2

Concentration and Washing of a High Volume T-Cell Culture

A high volume of allogenic T-cells from culture was processed for 100× concentration and 100× residual reduction using the cell harvester for the translational research market. The high volume disposable was used for this application to maximize the processing rate. The larger filter, tubing, and valve of this disposable supported process and permeate flow rates of 3000 and 300 mL/min, respectively. Step 2 rinsed the disposable with buffer. In step 3, 20 L of cells were concentrated from the source bag into the process loop using the continuous concentration method, Step 3. The relatively low first set-point of 1000 mL relative to the source volume required that this concentration step was performed while directing filter permeate to waste. This requirement extended the loading step relative to the similar procedure performed in Example 1. Step 4 provided a limited rinse of the source vessel. Two low volumes of buffer were sequentially directed to the source bag requiring additional concentration of the total volume in the process loop to maintain the 1000 mL setpoint. The rinse and rinse volumes provided a 3× dilution factor. In step 5, the cells were concentrated to the second setpoint of 500 mL. At this low volume, the wash step was performed extremely quickly due to the high filter permeate rate relative to the process loop volume. Step 6 provided an additional 16.7× dilution of soluble additives. In step 7 the process loop volume was reduced to the third setpoint of 100 mL before collecting cells in step 8. In step 9, the process loop was rinsed which resulted in the collection of 50 mL for each rinse and provided a combined 2× dilution factor for a total residual reduction factor of 100×. The final volume was 200 mL, 100× less than the initial sample volume. This procedure required approximately 100 minutes. Inclusion of set-up and removal steps of 1 and 10, respectively, is easily be achieved within the allotted 120 minutes.

Although the examples (Example 1 and 2) performed the same sequence of steps, the duration of time in an individual step was highly sample dependent. The control law enabled the hardware system to process of low and high volume samples without modification, but the requirement of a relatively low setpoint for the high volume sample extended the duration of step 3. However, the high processing rate used with the high volume sample relative to the second setpoint resulted in an accelerated washing procedure in step 6. The residual reduction factor was provided by a series of priming, rinse and wash steps. The user interface required the technician to define rinse and rinse volumes and the total residual reduction factor, thus enabling the calculation of the wash volume required in step 6 to achieve the desire level of residual dilution.

The processing steps executed are typically based on the given input source volume, the desired output volume, and/or the intermediate setpoints given. One example of the software implements a multithreaded state machine. The first thread implements the main process workflow steps. The second thread is used for sensor and fault monitoring. One example of the software assumes the following parameters are provided by the operator: estimate of the source volume, priming volume for the processing chamber, maximum allowable fluid transfer rates, filter feed rate, permeate rate percentage (as a function of filter feed rate), setpoint 1 (for step 3), setpoint 2 (for step 4b), setpoint 3 (for step 6), setpoint 4 (for step 7), number of rinses of the source bag, amount of buffer used for each rinse of the source bag, number of rinses of the processing chamber, amount of buffer used for each rinse of the processing chamber, dilution factor, final volume desired. The system detects the disposable kit type and checks the user input parameters against the following disposable values: minimum and maximum allowable filter feed rates, minimum and maximum allowable permeate rate percentage, hold up volume in section between turn valve and processing chamber, hold up volume in section between processing chamber and turn valve (filter loop), minimum and maximum allowable setpoints for processing chamber. Based on the disposable kit and the user input parameters, the system calculates the following parameters: estimated processing time, estimated amount of buffer required, setpoints and volumes required for individual steps.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:
1. A method of harvesting cells in an automated fashion from a fluidic material in a processing loop of a cell harvesting device comprising a processing chamber having an overall capacity, a filtering device, and a network of input and output lines each operatively coupled to one of a source pump, a buffer pump, and a permeate pump, said method comprising:
  circulating the fluidic material through the processing loop and maintaining the mass of the fluidic material in the processing chamber at a constant value defined as a setpoint, the maintaining step further comprising:

measuring a rate of change of a mass of the processing chamber;
directing the influx of the fluidic material by the source pump or the buffer pump;
estimating a permeate flux of the filtering device by:

$$q_{We}(t) = \gamma \omega_s(t) - \frac{dm_p(t)}{dt}, \text{ or}$$

$$q_{We}(t) = \beta \omega_W(t)$$

where $q_{We}(t)$ is the estimated permeate flux, $\omega_s(t)$ is the velocity of the source pump, $\gamma$ is a calibration constant of the source pump, $dm_p(t)/dt$ is the rate of change of the mass of the processing chamber, $\beta$ is a calibration constant of the permeate pump, and $\omega_W(t)$ is the Velocity of the Permeate Pump;
adjusting, in real time, a flow rate of the source pump or the buffer pump directing the influx based on the estimated permeate flux and a feedback term configured to adjust for errors or variations introduced by one or more system components of the cell harvesting device;
concentrating the cells by increasing permeate flux of the filtering device relative to the influx of the fluidic material into the processing chamber; and
collecting the concentrated cells in a collection chamber, wherein the fluidic material comprises a source material, a processing material or a combination thereof; and
wherein the flow rate through the source pump or buffer pump directing the influx, $q_{Sd}(t)$, is determined using a control law:

$$q_{Sd}(t) = q_{We}(t) - k\{m_p(t) - m_{pd}\}$$

where $m_{pd}$ is the setpoint, k>0 is a feedback gain, $q_{We}(t)$ is the estimated permeate flux, and $-k\{m_p(t)-m_{pd}\}$ is the feedback term.

2. The method of claim 1, wherein the processing material is selected from a liquid media, a buffer, or a combination thereof.

3. The method of claim 1, wherein the source material comprises cells in a liquid media or buffer.

4. The method of claim 1, wherein the source material has a total volume less than or equal to the overall capacity of the processing chamber, the method further comprising a prior step of loading the total volume of the source material to the processing loop.

5. The method of claim 1, further comprising a prior step of concentrating the source material when the source material has a total volume greater than a desired volume of the processing chamber, and wherein the desired volume of the processing chamber is less than or equal to the overall capacity of the processing chamber.

6. The method of claim 1, further comprising a prior step of washing the cells by introducing the fluidic material and balancing the influx of the fluidic material into the processing chamber with the permeate flux of the filtering device to maintain the mass of the fluidic material in the processing chamber at the constant value defined as the setpoint.

7. The method of claim 1, further comprising prior steps of introducing the processing material to the processing loop to rinse the processing loop before or after introducing the source material.

8. The method of claim 1, wherein the filtering device comprises a hollow fiber filter having a pore diameter in a range from about 0.1 to 1 pm and an inner fiber diameter of 200 to 2000 pm and a fiber count of 4 to 400.

9. The method of claim 1, wherein the processing loop is further operatively coupled to a source chamber and a buffer chamber and connections to the source chamber and buffer chamber comprise optical sensors to determine presence of a liquid in the connections.

10. The method of claim 9, further comprising introducing sterile air directly or indirectly to the source chamber, the buffer chamber or a combination of both.

11. The method of claim 1, wherein the method is independent of an initial sample volume of the fluidic material.

12. The method of claim 11, wherein the source material comprises cells in a liquid media or buffer.

13. The method of claim 11, further comprising loading the total mass of the source material to the processing loop prior to circulating the fluidic material, wherein the total mass of the source material is less than or equal to the overall capacity of the processing chamber.

14. The method of claim 11, further comprising concentrating the source material prior to circulating the fluidic material, when the source material has a total mass greater than the desired mass of the processing chamber.

15. The method of claim 11, further comprising washing the cells by introducing the fluidic material and balancing the influx of the fluidic material with the permeate flux of the filtering device to maintain the mass of the fluidic material in the processing chamber at the constant value.

16. The method of claim 11, further comprising a prior step of introducing the processing material to the processing loop to rinse the processing loop before or after introducing the source material.

17. A method of controlling a mass of a fluidic material in a processing chamber of a cell harvesting device in an automated fashion, wherein the cell harvesting device comprises a processing loop comprising a filtering device, the processing chamber, and a network of input and output lines each operatively coupled to one of a source pump, a buffer pump, and a permeate pump, the method comprising:
circulating the fluidic material through the processing loop and maintaining the mass of the processing chamber at a constant value defined as a setpoint, the maintaining step further comprising:
measuring a rate of change of a mass of the processing chamber;
estimating a permeate flux of the filtering device by:

$$q_{We}(t) = \gamma \omega_s(t) - \frac{dm_p(t)}{dt}, \text{ or}$$

$$q_{We}(t) = \beta \omega_W(t)$$

where $q_{We}(t)$ is the estimated permeate flux, $\omega_s(t)$ is the velocity of the source pump, $\gamma$ is a calibration constant of the source pump, $dm_p(t)/dt$ is the rate of change of the mass of the processing chamber, $\beta$ is a calibration constant of the permeate pump, and $\omega_W(t)$ is the velocity of the permeate pump; and
setting a flow rate through the source pump or the buffer pump, $q_{Sd}(t)$, which is determined using a control law:

$$q_{Sd}(t) = q_{We}(t) - k\{m_p(t) - m_{pd}\}$$

where $m_{pd}$ is the setpoint, k>0 is a feedback gain, $q_{We}(t)$ is the estimated permeate flux, and $-k\{m_p(t)-m_{pd}\}$ is a feedback term.

18. The method of claim 17, wherein the feedback term minimizes one or more errors in the estimation of the permeate flux, a source or buffer pump flux, an electrical noise, a mechanical noise or combinations thereof.

* * * * *